United States Patent [19]

Sher

[11] Patent Number: 5,592,866

[45] Date of Patent: Jan. 14, 1997

[54] ROTARY PISTON DRIVING MECHANISM

[76] Inventor: Arieh Sher, 35 Spinoza Street, Rehovot 76452, Israel

[21] Appl. No.: 473,880

[22] Filed: Jun. 7, 1995

Related U.S. Application Data

[63] Continuation of Ser. No. 100,949, Aug. 3, 1993, which is a continuation-in-part of Ser. No. 83,760, Jun. 30, 1993, Pat. No. 5,350,390, which is a continuation of Ser. No. 857,556, Mar. 25, 1992, abandoned.

[51] Int. Cl.⁶ ........................................................ F01B 3/00
[52] U.S. Cl. .................................. 92/31; 92/106; 74/129
[58] Field of Search ..................................... 92/31, 32, 33, 92/106; 74/128, 129

[56] References Cited

U.S. PATENT DOCUMENTS

| | | |
|---|---|---|
| 308,523 | 11/1884 | Sergeant . |
| 575,970 | 1/1897 | McCulloch . |
| 807,399 | 12/1905 | Rice, Jr. . |
| 1,173,326 | 2/1916 | Taylor et al. . |
| 1,623,411 | 4/1927 | Hulshizer . |
| 2,176,300 | 10/1939 | Fette . |
| 2,918,799 | 12/1959 | Geyer . |
| 3,766,952 | 10/1973 | Boers . |
| 3,911,793 | 10/1975 | Izumi . |
| 3,961,559 | 6/1976 | Teramachi . |
| 3,967,535 | 7/1976 | Rozansky . |
| 4,036,309 | 7/1977 | Petreev et al. . |
| 4,092,213 | 5/1978 | Nishimura . |
| 4,114,517 | 9/1978 | Teramachi . |
| 4,265,434 | 5/1981 | Hamilton et al. . |
| 4,274,327 | 6/1981 | Olsgaard . |
| 4,316,465 | 2/1982 | Dotson, Jr. . |
| 4,324,243 | 4/1982 | Helfgott et al. . |
| 4,351,516 | 9/1982 | Ersoy et al. . |
| 4,359,109 | 11/1982 | Truong-Cao . |
| 4,484,510 | 11/1984 | Hirzel . |
| 4,508,327 | 4/1985 | Ersoy . |
| 4,631,052 | 12/1986 | Kensey . |
| 4,674,500 | 6/1987 | DeSatnick . |
| 4,749,376 | 6/1988 | Kensey et al. . |
| 4,770,174 | 9/1988 | Luckman et al. . |
| 4,784,636 | 11/1988 | Rydell . |
| 4,790,813 | 12/1988 | Kensey . |
| 4,819,635 | 4/1989 | Shapiro . |
| 4,850,957 | 7/1989 | Summers . |
| 4,957,482 | 9/1990 | Shiber . |
| 5,005,468 | 4/1991 | Ulle . |
| 5,024,651 | 6/1991 | Shiber . |
| 5,047,008 | 9/1991 | deJuan, Jr. et al. . |

FOREIGN PATENT DOCUMENTS

| | | |
|---|---|---|
| 2645009 | 10/1990 | France . |
| 290306 | 9/1913 | Germany . |
| 581933 | 8/1933 | Germany . |
| 2344722 | 3/1974 | Germany . |
| 2446609 | 4/1976 | Germany . |
| 2516134 | 10/1976 | Germany . |
| 2652228 | 5/1978 | Germany . |
| 13081 | 2/1977 | Japan . |
| 190105 | 11/1982 | Japan . |
| 6-26503 | 11/1991 | Japan ........................................ 92/31 |
| 222095 | 7/1965 | U.S.S.R. . |
| 568753 | 11/1977 | U.S.S.R. . |
| 929932 | 5/1982 | U.S.S.R. . |
| 717413 | 2/1986 | U.S.S.R. . |
| 881099 | 11/1961 | United Kingdom . |
| 881099 | 11/1961 | United Kingdom ....................... 92/33 |
| 8204293 | 5/1984 | WIPO . |
| 8906517 | 1/1990 | WIPO . |

Primary Examiner—Thomas E. Denion

[57] ABSTRACT

A driving mechanism transforms continuous longitudinal reciprocation of a piston in a chamber into unidirectional rotation. The mechanism utilizes a closed wave-shaped groove defined in either the cylinder or the chamber and adapted to receive guiding members projecting from the other of the piston and the chamber. When the piston is forced to move longitudinally in either direction, the groove slides over the guiding members to force rotation. The apices of the wave-shaped groove are either contoured or provided with a gating structure to assure that the guide members do not backtrack but instead move in one direction through the groove.

15 Claims, 5 Drawing Sheets

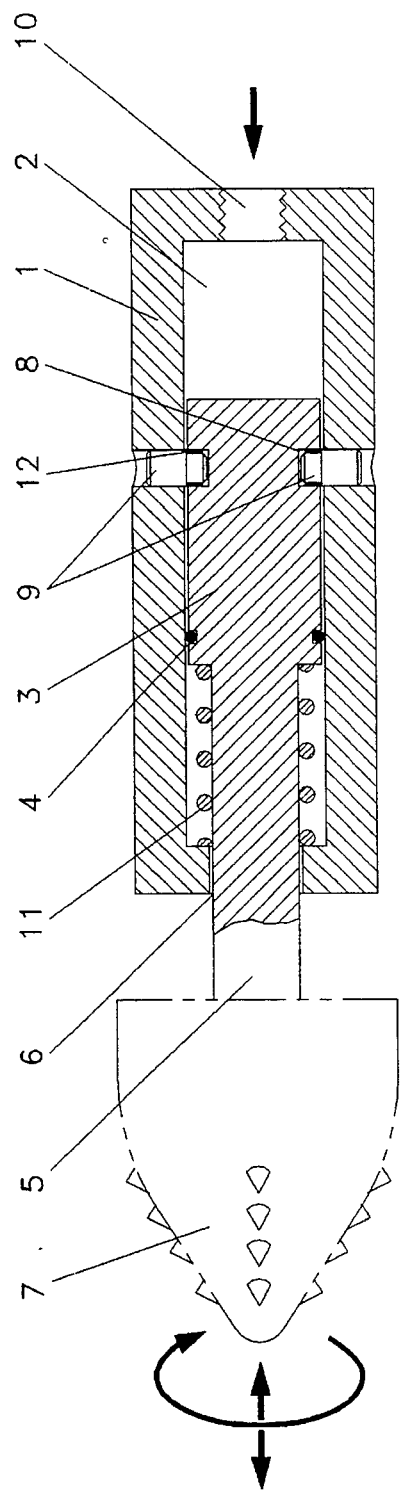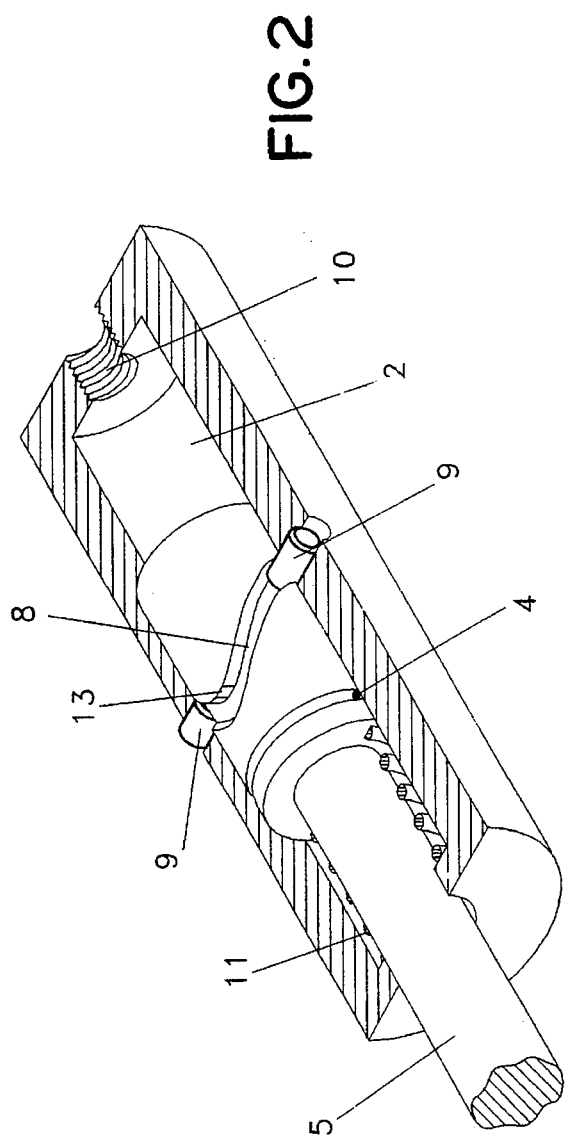

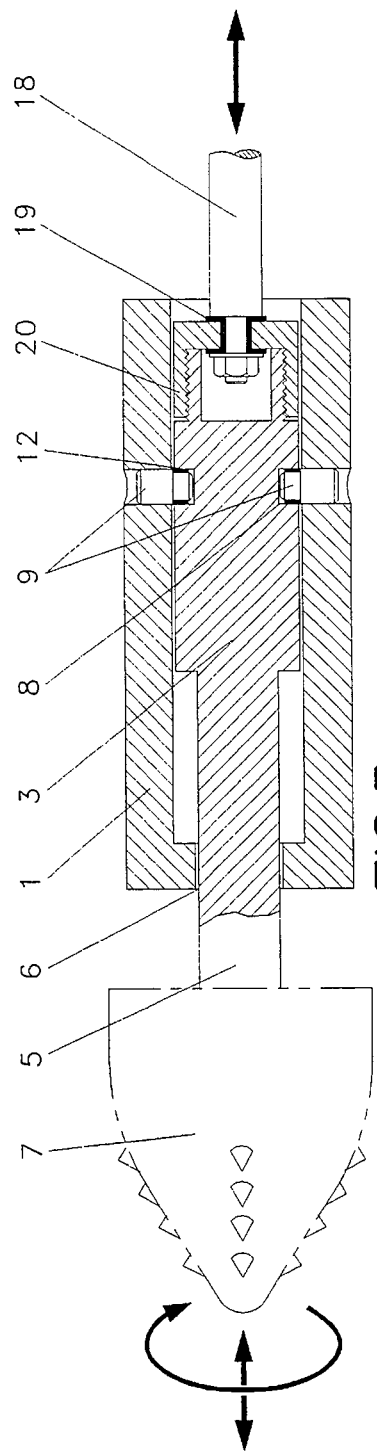
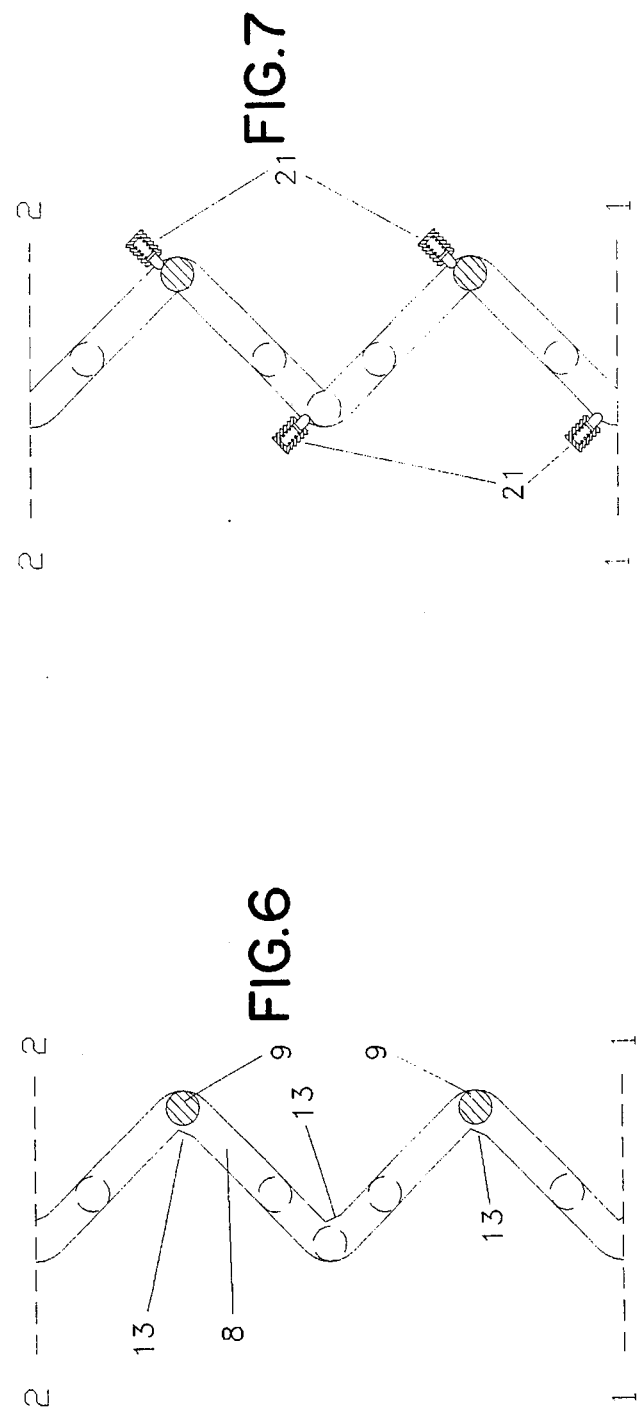

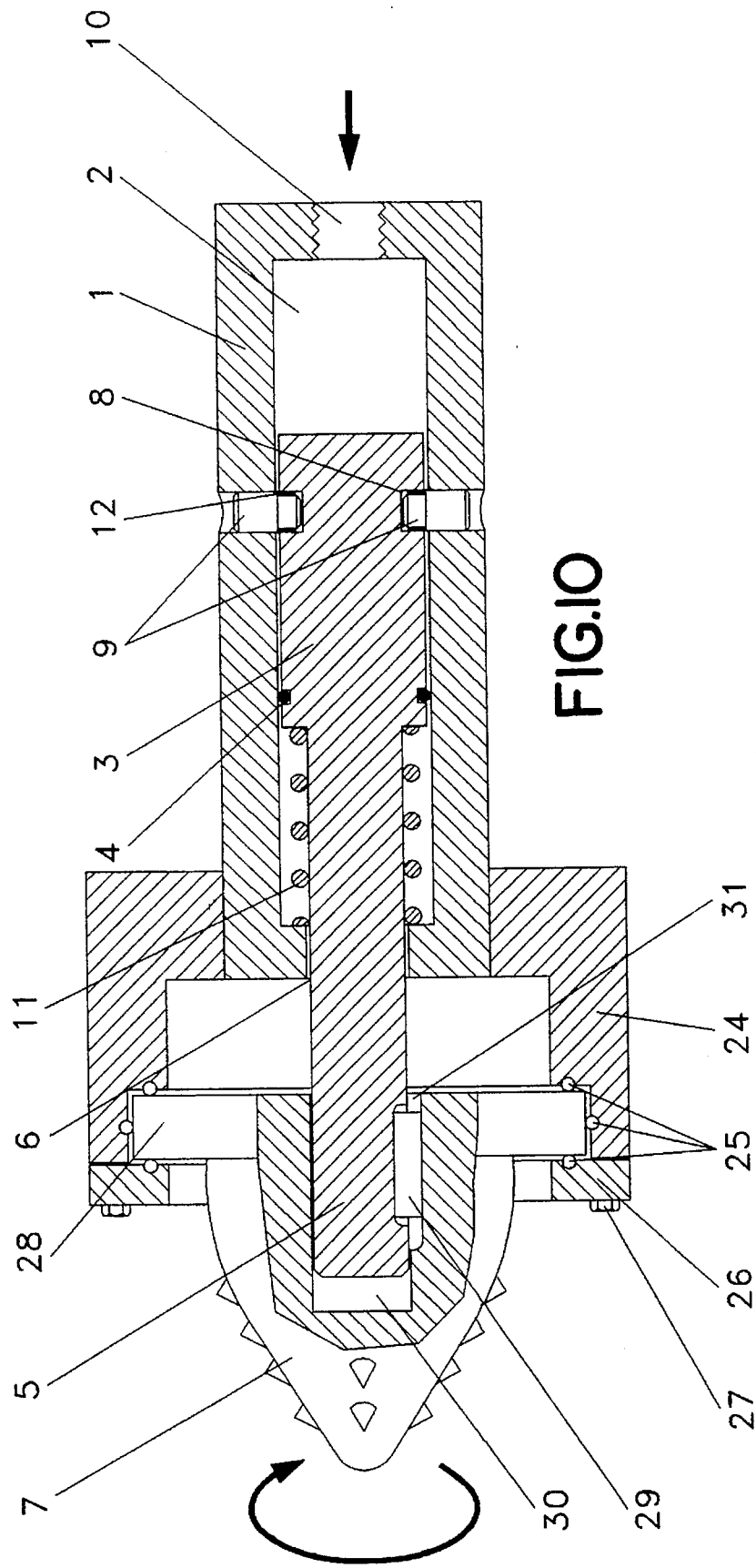

ROTARY PISTON DRIVING MECHANISM

CROSS-REFERENCE TO RELATED APPLICATION

This application is a continuation of co-pending U.S. patent application Ser. No. 08/100,949, filed Aug. 3, 1993, which is a continuation-in-part of my U.S. patent application Ser. No. 08/083,760, filed Jun. 30, 1993, now U.S. Pat. No. 5,350,390, which is a continuation of U.S. patent application Ser. No. 07/857,556, filed Mar. 25, 1992, now abandoned. The entire disclosures of those applications are expressly incorporated herein.

BACKGROUND OF THE INVENTION

1. Technical Field

The present invention relates to mechanisms for converting linear reciprocating motion to rotary motion and, more particularly, to such mechanisms wherein the resulting rotary motion is unidirectional. The invention has particular utility in applications where combined linear reciprocation and unidirectional rotation are required.

2. Discussion of the Prior Art

There is known in the prior art a certain type of mechanism for converting linear reciprocating to rotational oscillation. Such mechanisms are exemplified by the apparatus disclosed in the following documents: U.S. Pat. No. 1,173,326 (Taylor); U.S. Pat. No. 308,523 (Sergeant); U.S. Pat. No. 4,265,434 (Hamilton et al); U.S. Pat. No. 4,484,510 (Hirzel); International Publication No. WO82/04293 (Archer et al); and USSR Patent No. 222,095 (Kheyfets). Apparatus of this type includes a reciprocated piston, typically driven pneumatically or hydraulically, having a helical groove of defined length in its periphery. A guide member, such as a pin, ball or other projection, extends from the piston housing into the groove, forcing the piston to rotate about its axis in response to linear piston displacement. As the piston is linearly reciprocated, the guide member and groove arrangement causes the piston to rotate in a oscillatory manner; that is, the piston rotates in one direction in response to distal piston displacement, and in a second direction in response to proximal piston displacement.

For certain applications it is desirable to have continuous linearly reciprocating motion combined with unidirectional rotation, e.g., impact drills. The prior art mechanisms described above are incapable of rotating the piston in only one direction. On the other hand there are other prior art drive mechanisms that combine rotary movement and linearly reciprocating movement, but those mechanisms use continuous rotation movement as the primary movement to produce superimposed linear reciprocation.

OBJECTS AND SUMMARY OF THE INVENTION

It is an object of the present invention to provide a method and apparatus for rotating a piston in one direction in response to repetitive linear reciprocation of the piston.

It is another object of the present invention to provide a mechanism for converting repetitive linearly reciprocating movement to unidirectional rotational movement.

Still another object of the present invention is to provide a mechanism for converting linear reciprocation of the piston into unidirectional rotation of the piston, wherein the linear reciprocation is effected by fluid pressure requiring only a single fluid line.

A further object of the present invention is to provide a driving mechanism that transforms a continuous linear reciprocating movement into combined unidirectional rotation and reciprocation.

It is yet another object of the invention to provide a mechanism capable of rotating in accurately defined steps for use as a stepper motor.

It is also an object of the invention to provide a mechanism employing fewer components than prior art drive mechanisms with combined rotary and linear reciprocating movement.

In accordance with the present invention a linearly reciprocated piston is provided with an endless wave-shaped or zig-zag groove or channel in its periphery; i.e., the groove closes upon itself so as to have no defined ends. One or more guide members such as pins, bearing balls, etc., project from the surrounding cylindrical piston housing and ride in the groove, thereby causing the piston to rotate in response to linear piston displacement. The piston is caused to rotate in one direction either by geometrically configuring the groove or providing a mechanism to cause the piston to move through the groove in one direction only. Regardless of the type of arrangement, the piston rotates in that one direction in response to repetitive longitudinal reciprocation of the piston. A working head attached to the piston therefore moves in a similar manner to perform drilling, cutting, or other work functions. If desired, the working head can be decoupled from the piston rod in the longitudinal direction to produce rotation without linear reciprocation of the working head. In either case, unlike mechanisms such as crank shafts, the mechanism of the present invention permits rotation of the working head about an axis disposed concentrically with the longitudinal axis of reciprocation of the piston.

At the end of each longitudinal stroke of the piston, the guide member is located in an apex of the groove. Successive apices define respective angles through which the piston rotates during successive piston strokes. Accordingly, the mechanism of the invention is ideally suited for use in a stepper motor required to rotate in precise angular steps.

In one disclosed embodiment the piston is caused to rotate unidirectionally because of asymmetrical geometry near the apices of the groove. It is possible to render the configuration of the apices adjustable to change the asymmetry by 180° to thereby cause the piston to rotate in the opposite direction. The adjustment is typically made before the start of a cutting, drilling or other process and may be effected by mechanical, hydraulic or electrical means.

Linear or axial movement of the piston can be achieved by fluid power (liquid or gas) or by direct mechanical drive. Fluid drive may utilize either a single fluid line with a return spring or a differential pressure applied alternately at opposite ends of the piston.

BRIEF DESCRIPTION OF THE DRAWINGS

The above and still further objects, features and advantages of the present invention will become apparent upon considering the following detailed description of specific embodiments thereof, particularly when viewed in conjunction with the accompanying drawings wherein like reference numerals in the various figures are utilized to designate like components.

FIG. 1 is a view in longitudinal section of an embodiment of the rotary piston driving mechanism of the present invention.

FIG. 2 is a view in perspective and partial section of the mechanism of FIG. 1.

FIG. 5 is a view in longitudinal section of still another embodiment of the rotary piston driving mechanism of the present invention.

FIG. 6 is a partially diagrammatic planar projection view of one embodiment of the guide groove employed in the rotary piston driving mechanism of the present invention.

FIG. 7 is a partially diagrammatic planar projection view of a modified form of the guide groove employed with the rotary piston driving mechanism of the present invention.

FIG. 10 is a view in longitudinal section of yet another embodiment of the rotary piston drive mechanism of the present invention.

DESCRIPTION OF THE PREFERRED EMBODIMENTS

Figure 3:
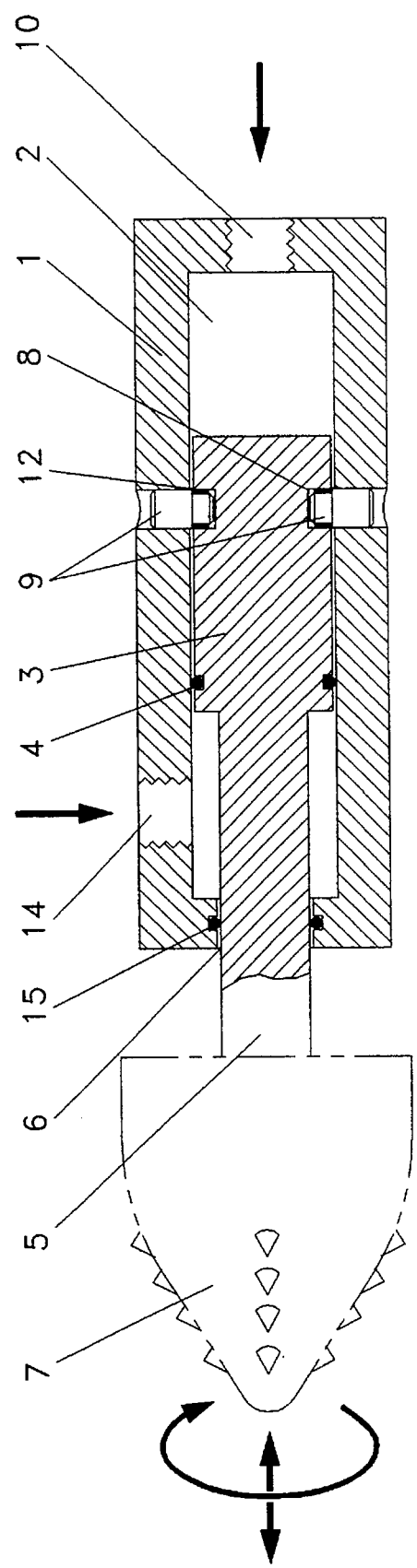
FIG. 3 is a view in longitudinal section of one alternative embodiment of the rotary piston driving mechanism of the present invention.

One embodiment of the rotary driving piston mechanism of the present invention is illustrated in FIGS. 1, 2 and 6 to which specific reference is now made. A housing 1 has an interior cylindrical chamber 2 with a piston 3 located and longitudinally movable in the chamber. The piston includes a reduced diameter rod 5 extending distally therefrom and out through a hole 6 defined in the distal end of the housing. An O-ring 4 or similar sealing member is disposed about the piston body to pressure-isolate the distal and proximal ends of chamber 2. Rod 5 is located in the distal chamber end.

The exposed distal end of rod 5 has a working head 7 secured thereto, the working head being represented with dashed lines in the drawing to indicate that the particular type of working head is not, of itself, part of the present invention. Working head 7 may be a cutting head, a drill bit, or any other working head required 1 to both reciprocate longitudinally and rotate unidirectionally.

An endless wave-shaped groove or channel 8 is defined in the surface of piston 3. Groove 8 extends continuously about the circumference of the piston and, in the illustrated embodiment, is made up of alternating forward sloping and rearward sloping sections intersecting at respective apices at the section junctions. One or more guide members 9 are secured and pressure sealed in respective angularly spaced bores in housing 1 and project radially inward into chamber 2. In particular, guide members 9 take the form of pegs or pins in the FIG. 1 embodiment and project into groove 8. In the illustrated embodiment two spaced pins 9 are provided at diametrically opposite locations across housing 1. It is to be understood that different numbers of such pins may be employed, as desired. It will be appreciated that, as piston 3 moves longitudinally in chamber 2, the pin and groove arrangement causes piston 3 to rotate about its longitudinal axis due to the tangential force components imparted by pins 9 to the walls of groove 8 that bear against the pins.

As best illustrated in the planar projection of groove 8 in FIG. 6, the groove has a substantially constant width and depth and is symmetrical about any plane longitudinally bisecting piston 3 and incorporating the central longitudinal axis of the piston. In FIG. 6 the dashed lines 1—1 and 2—2 constitute the same longitudinal line on piston 3. There are two complete waves in the illustrated groove 8, each wave occupying 180° of the piston circumference. The number of waves utilized in any groove depends upon and corresponds to the number of guide members 9 employed. The axial amplitude (i.e., the axial distance between successive opposite apices) of the sloped section of the groove depends upon the extent of longitudinal displacement of piston 3 in chamber 2. In particular, for longer reciprocation strokes of the piston, the longitudinal or axial amplitude must be correspondingly longer; for shorter strokes the amplitude must be shorter. The slope of the groove sections (i.e., their angle relative to the piston axis) is determined by both the amplitude and the pitch (i.e., the number of wave cycles). The ratio of piston longitudinal movement to angular movement during each stroke is determined by the pitch and amplitude.

In the FIG. 6 embodiment guide groove 8 is configured to have each pair of successive groove sections disposed symmetrically about a longitudinal line drawn through the apex joining that pair of sections. In addition, the slope of each groove section is constant throughout the length of that section. The symmetry causes the angle of piston rotation to be the same during successive longitudinal piston strokes. The constant slope causes the rotation to be at a constant angular rate or speed during a stroke. It will be understood, however, that these end results may not be required for all applications of the present invention. Accordingly, different groove sections may include the same or different curves and bends to change the angular speed during particular piston strokes. Likewise, successive groove sections need not be symmetrical about their joining apex to thereby permit different angular rotation behavior during successive strokes. The nature of the curves and bends in any groove section may take almost any configuration with certain restrictions. First, the bend cannot be such as to cause the piston rotation direction to reverse; and second, the groove section cannot have a configuration that causes guide member 9 to backtrack through a portion of the section (i.e., reverse directions in that portion). As to avoiding backtracking, a precluded or impermissible configuration would be one where, instead of an apex, two sloped groove sections meet at a third longitudinal section through which the guide members move first in one direction at the end of a piston stroke and then backtrack and move in the reverse direction at the start of the next piston stroke.

A flow port 10 is defined in the upstream end of housing 1. Port 10 is threaded to receive a suitably threaded connector of a flow line capable of delivering sequential pulses of pressurized fluids (e.g. liquid or gas) into the upstream end of chamber 2. In the downstream portion of the chamber there is a resilient bias member such as a helical spring 11 wound about rod 5 with its ends abutting piston 3 and the downstream wall of chamber 2. Specifically, the transition between rod 5 and the larger diameter piston 3 forms a distally facing annular shoulder on the distal end of the piston against which one end of spring 11 abuts. The other end of the spring abuts the annular portion of the distal end wall of chamber 2 surrounding hole 6.

Application of a positive pressure pulse to the proximal end of chamber 2 via port 10 drives piston 3 in a distal direction against the bias force of spring 11. Groove 8 is forced to ride along guide pins 9 to consequentially cause piston 3 to rotate as it moves distally. Upon termination of the pressure pulse, the bias force exerted by spring 11 forces piston 3 in a proximal direction. This is aided by the negative pressure created on the proximal side of the piston by removal of the pressure pulse. Again, longitudinal movement of the piston forces groove 8 to ride along guide pins 9, causing the piston to rotate. Suitable low friction bearings 12 are disposed about portions of pins 9 within groove 8 to facilitate movement of the pins through the groove.

In the following description the surfaces of the groove side walls are described as load bearing and non-load bearing. The load bearing surface corresponds to the wall forced against pins 9 as the piston is moved in one or the other longitudinal direction. For example, when the piston is being forced distally, the proximal groove wall is load bearing while the distal groove wall is non-load bearing. In order to force the piston to rotate in one direction irrespective of its direction of longitudinal movement, the apices of groove 8 are specially contoured. In particular, the load bearing side wall of the groove at each apex is radiused to facilitate unidirectional motion of the pins beyond the apex. The resulting arcuate configuration is symmetrical with respect to the piston longitudinal axis. On the other hand, the non-load bearing wall of the groove at the apex is asymmetrically configured to assure continued forward movement of piston 9 through the apex as the piston changes longitudinal direction. In particular, the non-load bearing surface at the apex has a more sudden directional transition; that is, it is more pointed rather than arcuate and is positioned ahead of the opposite radiused load bearing wall. By "ahead of" it is meant that pin 9, in approaching the end of a sloped groove section, passes slightly beyond the point in the non-load bearing wall before reaching the middle of the arc in the opposite radiused load bearing wall where the wall effectively redirects the pin into the next channel section. Accordingly, as the longitudinal direction of the piston changes and causes the opposite wall of the groove to become load bearing, pins 9 have moved sufficiently beyond the point in that wall to cause the pins to be directed into the next groove section. In order to further facilitate this advancement of the pins into the next groove section, a short segment 13 of the new load bearing wall is sloped at a larger angle to the piston axis than is the rest of the groove section to thereby guide the pin into that groove section. Segment 13 thus serves as a camming surface to direct the pin forwardly through the groove, and is positioned in longitudinal alignment with the center of the arc of the opposite groove wall.

Since the opposite walls of groove 8 alternatively serve as load bearing and non-loading bearing surfaces, their configurations at successive groove apices alternate from radiused and symmetrical to pointed and asymmetrical.

As a consequence of (a) the piston 3 being reciprocated longitudinally by the applied pressure pulses and the return spring bias, and (b) the unidirectional rotation of the piston in response to longitudinal reciprocation, working head 7 moves longitudinally back and forth while rotating in one direction.

The embodiment illustrated in FIGS. 1 and 2 has pins 9 located in housing 1 and projecting into a groove 8 defined in the surface of piston 3. It will be appreciated, however, that the pins can also be located in the piston and project into a similar groove defined in the chamber wall.

In an embodiment illustrated in FIG. 3, the bias spring is removed and in its place there is a second fluid flow port 14 communicating with the distal end of chamber 2. Fluid pressure is applied differentially between ports 10 and 14 in a cyclical manner to cause piston 3 to move first in one direction and then the other longitudinally in chamber 2. An O-ring 15 is provided in the distal hole 6 of housing 1 to provide a seal against rod 6 so as to assure no loss of fluid pressure in the distal end of the chamber. The source of alternating differential pressure may be a conventional shuttle valve, a fluidic oscillator, or any conventional source of differential pressure pulses.

Figure 4:
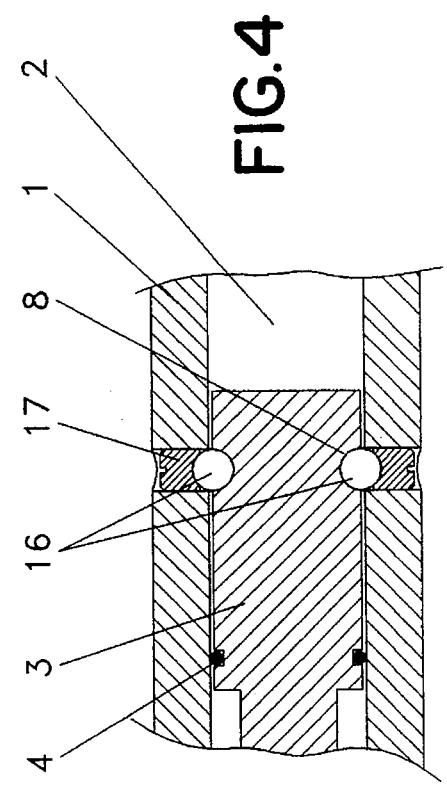
FIG. 4 is a detailed view in longitudinal section of a portion of a still further embodiment of the rotary piston driving mechanism of the present invention.

The embodiment illustrated in FIG. 4 shows the guide pins replaced by bearing balls 16 secured in their respective bores by set screws 17, or the like. The use of bearing balls 16 as guide members reduces friction to facilitate piston movement.

As illustrated in FIG. 5, a further embodiment of the invention has the reciprocating longitudinal force for the piston developed by a prime mover such as a reciprocating motor (not shown) having a drive rod 18 extending therefrom and secured to a cup-shaped adapter 20 threadedly engaging a threaded proximal end fitting of piston 3. In this embodiment the housing is open at its proximal end, and there is no pressure seal about rod 6 in distal hole 6. A suitable bearing 19 extends through a hole in the proximal end of adapter 20, and rod 18 is secured to the bearing inside the adapter by an appropriate nut or the like engaging the threaded distal end of the rod.

FIG. 7 is a view similar to FIG. 6 but showing an alternative arrangement for facilitating continued forward motion of the guide members 9 through groove 8. In particular, a spring loaded pin 21 having a smoothly curved distal end projects into groove 8 through the load bearing wall at the end of each groove section and just prior to the curvature in the radiused wall of the apex. One such spring loaded pin 21 is provided at the end of each groove section. As the guide member moves through the groove section it is urged against the load bearing wall and directs a reactive force component against that wall. Upon the guide member reaching the curved end of the pin, this reactive force operates in opposition to the bias spring to depress pin 21 into its recess and permit the guide member to smoothly pass the pin. Once the guide member has passed the pin, the bias force of the spring forces the pin back into the groove. The direction of the bias force on pin 21 is into the next groove section and substantially perpendicular to the groove section just traversed. Upon change in the longitudinal direction of the piston, the opposite surface of the groove becomes load bearing so that the reactive force from the guide member is directed against that surface but not against the opposite surface through which pin 21 projects. Accordingly, the pin is not forced back into its recess but instead serves to block any attempt by the guide member to back track into the previously traversed groove section. In addition, the spring loaded pin 21 acts on the guide members 9 to force those members into the next groove section. Pins 21 thus serve as forcing members and gates to cause passage of the guide members in one direction only through groove 8.

Figure 9:
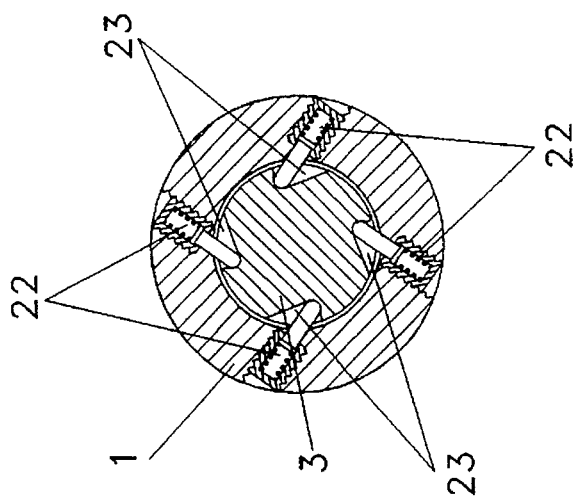
FIG. 9 is a view in transverse section taken along lines A—A of FIG. 8.
Figure 8:
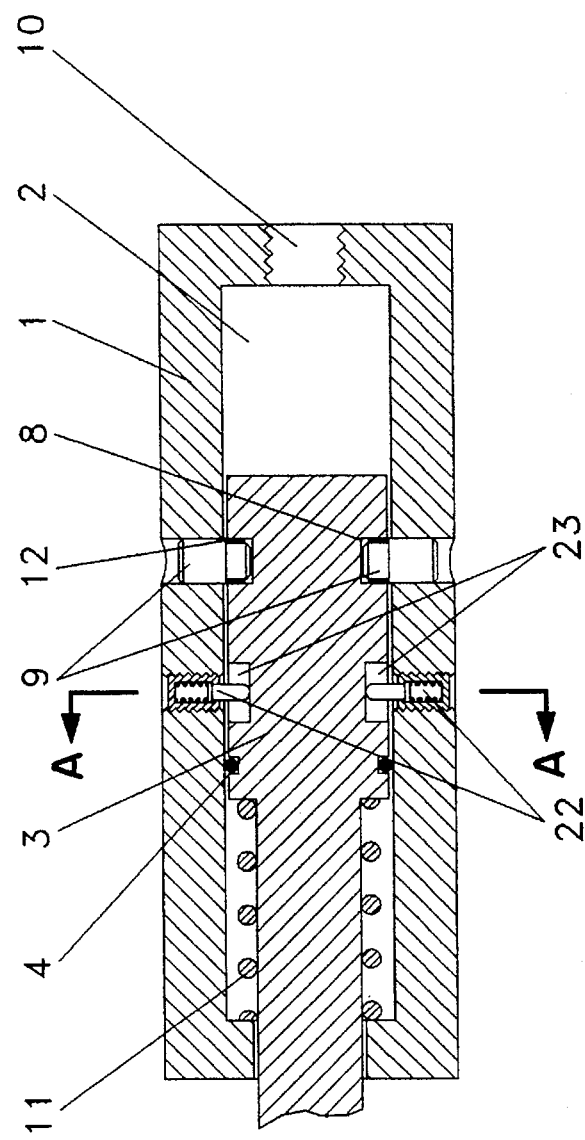
FIG. 8 is a view in longitudinal section of a portion of a further embodiment of the rotary piston driving mechanism of the present invention.

In the embodiments described thus far, the structure or contouring required to assure unidirectional motion of guide members 9 or 16 through groove 8 is located at or in the groove itself. This is not mandatory. For example, with reference to FIGS. 8 and 9, a plurality of depressions 23 may be defined in the piston periphery at a location longitudinally spaced from guide groove 8. A plurality of spring loaded drive pins 22 are disposed in respective recesses at spaced angular locations in housing 1 and are arranged to project into drive depressions 23. Importantly, drive pins 22 do not project radially into depressions 23 but instead project at an angle between radial and tangential, generally in the direction of desired piston rotation. The diameter or width of drive pins 22 is sufficiently smaller than the width of depressions 23 to permit longitudinal reciprocation of the piston without interference from drive pins 22 in the depressions.

The depth of depressions 23 is contoured to permit the spring loaded drive pins 22 to force piston 3 to rotate in the desired direction. Depressions 23 have shallow segments sufficiently shallow to force drive pins 22 to retract into their respective recesses in housing 1 when the shallow segments are radially aligned with the pins. In this regard the angular spacing between the shallow depression segments corresponds to the angular spacing between pins 22 so that all shallow segments are simultaneously aligned with respective pins 22. The depressions include a relatively short leading edge extending from the rear of the preceding shallow segment into the piston in a direction close to radial. This short leading edge terminates at the nadir or deepest part of the depression where the depression begins to smoothly curve into a trailing edge. The trailing edge is significantly longer than the leading edge and extends toward the next shallow segment at a much less abrupt angle than the leading edge. As piston 3 rotates under the impetus of guide members 9 in guide groove 8, the depressions 23 reach respective drive pins 22 at the same time guide members 9 are received in respective apices in guide groove 8. The previously recessed drive pins 22 spring or snap into the depressions, exerting forces on the sharp leading edges of the depressions in a manner to aid continued rotation of the piston in the desired direction. After passing the nadir portion of the depression the drive pins are forced back into their respective recesses by the gradually sloped trailing edges of the depressions acting on the pins in a cam-like manner. In effect, the trailing edges act like ramps along which pins 22 ride as they are being gradually retracted against their bias springs into their recesses. Pins 22 cannot effectively force the trailing depression edges in the wrong rotation direction because the ramp is angled in the wrong direction to do so and, more importantly, because the guide pins 9 are already beyond the guide channel apices and are forcing the piston in the intended rotation direction. The overall effect is to urge the piston continuously in the desired rotation direction.

Referring now to FIG. 10, another embodiment of the invention is characterized by the working head 7 being attached to the piston rod 5 in a manner whereby the working head rotates with the piston but does not reciprocate longitudinally therewith. In particular, piston rod 5 has its distal end disposed in a centered axial bore 30 at the proximal end of working head 7. A key 29 secured to the distal portion of rod 5 is longitudinally slidable in a thin longitudinally-extending slot 31 defined in the working head and communicating with the periphery of bore 30 along one side of the bore. Key 29 thus engages the working head 7 in slot 31 to cause rod 5 and the working head to rotate together. However, rod 5 is free to move longitudinally (i.e., axially) relative to the working head 7 to the extent of the permitted longitudinal movement of key 29 in slot 31.

Projecting radially from and fixedly secured to working head 7 at diametrically opposed locations is an annular flange 28. Projecting forwardly and fixedly secured to housing 1 is a generally annular bracket 24. Bracket 24 extends longitudinally along the proximal end of working head 7 and includes an annular recess opening toward the working head and configured to receive flange 28. The forward side of the bracket recess is closed by an annular plate 26 secured by screws 27 to the distal end of bracket 24. The thickness of flange 28 is but slightly smaller than the width of the bracket, both of which dimensions extend longitudinally relative to the piston rod 5. Multiple ball bearings 25 are disposed between flange 28 and the facing surfaces in the bracket recess and plate 26 to facilitate rotary sliding movement of the flange in the recess and to prevent both radial and axial movement of the flange in the recess. Flange 28, while rotating with working head 7 about the longitudinal axis of rod 5, thus passes smoothly through the bracket recess. Accordingly, flange 28 and its attached working head 7 are precluded from moving longitudinally relative to bracket 24 and the attached housing 1, but the working head is free to rotate relative to housing 1. Thus, when piston 3 and rod 5 are reciprocated within housing 1 in the manner described above, rod 5 moves within bore 30 but does not move the working head longitudinally relative to housing 1. The working head, therefore, only rotates with piston rod 5 in response to linear reciprocation of the piston, and the resulting rotation is unidirectional.

Although embodiments are disclosed wherein the guide members are pins 9 or bearing balls 16, guide members having other configurations are certainly within the scope of the present invention. Likewise, although a variety of techniques for reciprocating piston 3 are disclosed herein, the scope of the invention incorporates substantially any technique for producing such reciprocation.

A wide variety of wave-shapes may be utilized for the guide groove or channel 8, but there are certain restrictions on the groove configuration. First of all, the groove must be endless; that is, the groove must continue around the entire periphery of the piston and close upon itself. Second, the groove must permit unidirectional motion of the guide members therethrough. In this regard, the apices of the wave-shape may be geometrically configured in any manner that will guide the guide members in the forward direction and preclude backtracking through a previous groove section. Alternatively, a structural member, similar to the spring loaded pin gate described herein, may be provided at the various apices. Other techniques for preventing backtracking of the guide members in the channel and forcing forward motion of the piston may be utilized within the scope of the invention. Further, as noted above, the individual groove sections may tend to achieve desired rotation effects, and the groove sections may each have different configurations.

Another consideration relating to the configuration of groove 8 is the fact that there must be no longitudinal projections of the groove extending from the wave shape that would cause termination of the rotation by causing the guide members to move longitudinally relative to the piston at one or more points during the guide member movement about the piston periphery. For example, in U.S. Pat. No. 4,508,327 (Ersoy) there is disclosed a swing clamp wherein a longitudinally reciprocated piston has a guide channel extending about its periphery and receiving guide members for producing rotation of the piston in response to the longitudinal reciprocation. However, the guide channel has longitudinally extending segments at its section junctions for terminating rotation of the piston during a portion of each longitudinal displacement as the guide members backtrack in the longitudinal extensions. Moreover, some of these extensions are open to permit the piston to be removed from the housing. The purpose of the present invention, on the other hand, is not to serve as a clamp but to provide unidirectional rotation of the piston in response to continuous piston longitudinal reciprocation. To achieve this result the guide grooves of the present invention have no open ends, have apices that permit continued rotation as the longitudinal direction of the reciprocating piston changes, and prevent backtracking of the guide members through any part of the groove. Accordingly, the described constraints on the configuration of the guide groove 8 of the present invention are important aspects of the invention.

It is to be understood that to achieve the smoothest possible rotation of piston 3, the duration of application of the longitudinal driving force for each linear stroke of the piston should be synchronized with the time required for guide members 9, 16 to travel between successive apices in guide channel 8. In other words, if the longitudinal driving force remains after the guide members reach the apices, rotation stops until the longitudinal force reverses. On the other hand, if the longitudinal force is reversed too soon (i.e., before the guide members reach the apices), the rotation reverses because the guide members are forced to change direction in the guide groove; this is impermissible for the present invention. Proper synchronization of the longitudinal driving force duration and the guide member transit time between apices may be achieved in any of numerous ways. For example, it is quite simple to determine, either empirically or theoretically, the time required for the guide members to travel between apices in response to a given force level, and then apply such force level for the determined time. Alternatively, the duration of longitudinal force application may be automatically controlled by sensors associated with the piston and/or housing to provide a signal as the piston approaches the maximum displacement positions. Such sensors may use magnetic, electronic, fluidic or any other media conventionally employed for position sensing.

From the foregoing description it will be appreciated that the present invention makes available a novel rotary piston driving mechanism wherein a longitudinally reciprocating piston is caused to rotate in only one direction irrespective of longitudinal directional changes of the driving force.

Having described preferred embodiments of a new and improved rotary piston driving mechanism constructed in accordance with the present invention, it is believed that other modifications, variations and changes will be suggested to persons skilled in the art in view of the teachings set forth herein. It is therefore to be understood that all such variations, modifications and changes fall within the scope of the present invention as defined by the appended claims.

What is claimed is:

1. Apparatus for converting longitudinal reciprocating motion of a piston in a housing to combined longitudinal reciprocation and rotation of the piston in only one rotational direction about its longitudinal axis, said apparatus comprising:

an endless wave-shaped guide groove defined in one of said piston and said housing and comprising a series of groove sections of generally alternating directions;

motion conversion means responsive to linear motion of said piston in said housing for causing said piston to also rotate relative to said housing about said axis, said motion conversion means comprising at least one guide member secured in the other of said piston and said housing and projecting substantially radially and into said guide groove;

directing means responsive to continuously repeated linear reciprocation of said piston for directing said guide member in a forward direction into successive groove sections while preventing reverse directional movement of the guide member into a groove section that has been immediately previously traversed; and a working head secured to said piston for rotational and reciprocating movement with said piston.

2. The apparatus of claim 1 wherein said working head is disposed outside said housing.

3. The apparatus of claim 2 wherein said working head is a drill bit.

4. The apparatus of claim 1 further comprising drive means for reciprocating said piston longitudinally in said housing, said drive means comprising a fluid actuator for applying successive pulses of pressurized fluid to force said piston in a first longitudinal direction; and resilient means for urging said piston in a second longitudinal direction opposite said first longitudinal direction.

5. The apparatus of claim 1 further comprising drive means for reciprocating said piston in said housing, said drive means comprising a fluid actuator for applying pulses of fluid differentially to opposite ends of said piston.

6. The apparatus of claim 1 further comprising drive means for reciprocating said piston longitudinally in said housing, said drive means comprising a direct mechanical drive.

7. The apparatus of claim 1 wherein said directing means includes an asymmetrical geometric configuration of the closed wave-shaped groove for urging said guide member in only a forward direction in said groove.

8. The apparatus of claim 1 wherein said directing means comprises a mechanism operating directly on said conversion means to allow only a unidirectional rotational motion of the piston.

9. The apparatus of claim 1 wherein said directing means comprises a mechanism engaging said piston and said housing at a location longitudinally spaced from said groove and said guide member to allow only unidirectional rotational motion of said piston.

10. A method of converting longitudinal reciprocating motion of a piston in a housing into combined reciprocating and continuous unidirectional rotating motion of a shaft extending externally of said housing, said method comprising the steps of:

(a) applying force to a first end of said piston to provide continuously repeated longitudinal reciprocating motion of said piston;

(b) projecting a shaft from a second end of said piston opposite said first end externally of said housing;

(c) defining a guide channel in one of said piston and said housing;

(d) projecting a guide member into engagement with said guide channel from the other of said piston and said housing;

(e) directing piston, by means of the engagement between said guide member and said guide channel, to non-intermittently rotate in only one direction in response to said piston continuously reciprocating longitudinally irrespective of longitudinal direction changes of said piston; and (f) securing said shaft to said piston to assure that said shaft continuously reciprocates and non-intermittently rotates in only said one direction with said piston.

11. The method of claim 10 further comprising the step of:

(g) securing a working head to said projecting shaft.

12. The method of claim 11 wherein step (g) includes securing a drill bit to said projecting shaft.

13. The method of claim 11 wherein step (a) comprises applying a series of fluid pressure pulses to said piston.

14. The method of claim 11 wherein step (g) comprises the step of securing said working head to said piston to cause said working head to rotate with said piston but preventing said working head from reciprocating longitudinally with said piston.

15. Apparatus for converting linear reciprocating motion of a piston in a housing to rotation of the piston in only one direction about its longitudinal axis, said apparatus comprising:

an endless wave-shaped guide groove defined in one of said piston and said housing and comprising a series of groove sections of generally alternating directions;

motion conversion means responsive to linear motion of said piston in said housing for causing said piston to rotate relative to said housing about said axis, said motion conversion means comprising at least one guide member secured in the other of said piston and said housing and projecting substantially radially and into said guide groove; and directing means responsive to linear reciprocation of said piston for directing said guide member in a forward direction into circumferentially successive groove sections while preventing reverse directional movement of the guide member into a groove section that has been immediately previously traversed;

wherein each successive pair of said groove sections intersects at a respective apex, and wherein successive apices point in generally opposite longitudinal directions;

wherein said groove has first and second opposite side walls, wherein said guide member alternately bears forcefully against said first and second side walls in successive sections of said groove to define load bearing and non-load bearing side walls in each groove section, and wherein said directing means comprises:

at each apex on the load bearing side wall, a smooth arcuate section positioned symmetrically with respect to the longitudinal axis of the piston for effecting smooth redirected movement of the guide member therealong into the next successive groove section in said forward direction;

at each apex on the non-load bearing side wall, a discrete directional transition positioned asymmetrically with respect to the longitudinal axis of the piston so as to be passed by said guide member in said groove before said guide member is redirected into the next successive groove section by said symmetrical arcuate section; and a drill bit disposed outside said housing and secured to said piston for reciprocal and rotational movement with said piston.

* * * * *